(12) United States Patent
El-Nounou et al.

(10) Patent No.: US 7,951,413 B2
(45) Date of Patent: May 31, 2011

(54) CATHETER BALLOON HAVING A LUBRICIOUS COATING

(75) Inventors: Fozan El-Nounou, Santa Clara, CA (US); Timothy Owens, Dublin, CA (US); Florencia Lim, Union City, CA (US); Edwin Wang, Tustin, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1260 days.

(21) Appl. No.: 11/582,580

(22) Filed: Oct. 18, 2006

(65) Prior Publication Data

US 2007/0032760 A1 Feb. 8, 2007

Related U.S. Application Data

(62) Division of application No. 10/382,330, filed on Mar. 5, 2003, now Pat. No. 7,172,575.

(51) Int. Cl.
*B05D 3/10* (2006.01)
*B32B 3/26* (2006.01)
*A61M 25/10* (2006.01)

(52) U.S. Cl. ....... 427/2.28; 427/2.1; 427/2.24; 427/532; 428/304.4; 428/306.6; 428/421

(58) Field of Classification Search .............. 427/2.1, 427/2.24, 2.25, 532; 428/304.4, 306.6, 308.4, 428/421
See application file for complete search history.

(56) References Cited

U.S. PATENT DOCUMENTS

| | | | |
|---|---|---|---|
| 4,055,682 A | 10/1977 | Merrill | |
| 4,946,903 A | 8/1990 | Gardella, Jr. et al. | |
| 5,061,738 A | 10/1991 | Solomon et al. | |
| 5,118,524 A | 6/1992 | Thompson et al. | |
| 5,437,900 A | 8/1995 | Kuzowski | |
| 5,496,276 A * | 3/1996 | Wang et al. | 604/103.06 |
| 5,891,114 A | 4/1999 | Chien et al. | |
| 5,932,299 A | 8/1999 | Katoot | |
| 6,120,477 A * | 9/2000 | Campbell et al. | 604/96.01 |
| 6,270,902 B1 | 8/2001 | Tedeschi et al. | |
| 6,946,173 B2 * | 9/2005 | Lim et al. | 428/35.2 |
| 2002/0146557 A1 * | 10/2002 | Claude et al. | 428/336 |

* cited by examiner

*Primary Examiner* — Timothy H Meeks
*Assistant Examiner* — Cachet I Sellman
(74) *Attorney, Agent, or Firm* — Fulwider Patton LLP

(57) ABSTRACT

A balloon for a catheter and a method of making the balloon, having a layer of a porous polymeric material with a modified outer surface and a lubricious coating bonded to the modified outer surface. In one embodiment, the modified outer surface is formed by a polymer impregnated in the porous polymeric material, and the subsequently applied lubricious coating bonds to the impregnating polymer. In another embodiment, the modified outer surface is formed by a functionality deposited on the porous polymeric material which bonds to the subsequently applied lubricious coating. The modified outer surface provides an improved strong bond between the lubricious coating and the balloon, for improved catheter performance.

8 Claims, 2 Drawing Sheets

CATHETER BALLOON HAVING A LUBRICIOUS COATING

This application is a division of U.S. Ser. No. 10/382,330, filed Mar. 5, 2003, now U.S. Pat. No. 7,172,575.

BACKGROUND OF THE INVENTION

This invention generally relates to medical devices, and particularly to intracorporeal devices for therapeutic or diagnostic uses, such as balloon catheters.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of a dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with fluid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant a stent inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion. Stent covers on an inner or an outer surface of the stent have been used in, for example, the treatment of pseudo-aneurysms and perforated arteries, and to prevent prolapse of plaque. Similarly, vascular grafts comprising cylindrical tubes made from tissue or synthetic materials such as polyester, expanded polytetrafluoroethylene, and DACRON may be implanted in vessels to strengthen or repair the vessel, or used in an anastomosis procedure to connect vessels segments together.

In the design of catheter balloons, characteristics such as strength, compliance, and profile of the balloon are carefully tailored depending on the desired use of the balloon catheter, and the balloon material and manufacturing procedure are chosen to provide the desired balloon characteristics. A variety of polymeric materials are conventionally used in catheter balloons. Use of polymeric materials such as PET that do not stretch appreciably consequently necessitates that the balloon is formed by blow molding, and the deflated blow molded balloon forms wings which are folded around the catheter shaft prior to inflation of the balloon in the patient's body lumen. However, it can be desirable to employ balloons, referred to as formed-in-place balloons, that are not folded prior to inflation, but which are instead expanded to the working diameter within the patient's body lumen from a generally cylindrical or tubular shape (i.e., essentially no wings) that conforms to the catheter shaft.

A catheter balloon formed of expanded polytetrafluoroethylene (ePTFE) has been suggested. ePTFE is PTFE which has been expanded to form porous ePTFE which typically has a node and fibril microstructure comprising nodes interconnected by fibrils. However, ePTFE has proven difficult to bond to surface coatings.

It would be a significant advance to provide a catheter balloon, or other medical device component, with improved performance and bondability.

SUMMARY OF THE INVENTION

This invention is directed to a balloon for a catheter and a method of making the balloon, having a layer of a porous polymeric material with a modified outer surface and a lubricious coating bonded to the modified outer surface. In one embodiment, the modified outer surface is formed by a polymer impregnated in the porous polymeric material, and the subsequently applied lubricious coating bonds to the impregnating polymer. In another embodiment, the modified outer surface is formed by a functionality deposited on the porous polymeric material which bonds to the subsequently applied lubricious coating. The modified outer surface provides an improved strong bond between the lubricious coating and the balloon, for improved catheter performance.

A catheter balloon of the invention is suitable for use in a variety of balloon catheters, including coronary and peripheral dilatation catheters, stent delivery catheters, drug delivery catheters, and the like. A balloon catheter of the invention generally comprises an elongated shaft having a proximal end, a distal end, and at least one lumen, and a balloon on a distal shaft section with an interior in fluid communication with the at least one lumen of the shaft. The balloon has a proximal skirt section bonded to the shaft, a distal skirt section bonded to the shaft, and an inflatable section therebetween. In a presently preferred embodiment; the balloon has a first layer (i.e., the porous polymeric layer), and second layer, extending from the proximal skirt section to the distal skirt section, with the second layer preferably being an inner layer relative to the porous polymeric first layer of the balloon. The catheter shaft typically comprises an outer tubular member defining the inflation lumen, and an inner tubular member defining a guidewire lumen extending at least within a distal shaft section, with the balloon proximal skirt section bonded to a distal portion of the outer tubular member and the balloon distal skirt section bonded to a distal portion of the inner tubular member. However, a variety of suitable catheter configurations can be used as are conventionally known, including dual lumen designs. The balloon catheter can be an over-the-wire type catheter with a guidewire lumen extending from the proximal to the distal end of the catheter, or alternatively a rapid exchange type catheter with a distal guidewire port in a distal end of the catheter, a proximal guidewire port in a distal shaft section located distal of the proximal end of the shaft and typically spaced a substantial distance from the proximal end of the catheter, and a short guidewire lumen extending between the proximal and distal guidewire ports in the distal section of the catheter.

In a presently preferred embodiment, the porous polymeric material is expanded polytetrafluoroethylene (ePTFE), including ePTFE available from Zeus, Atrium Medical, Inertech, and IPE, and typically having an initial porosity of at least about 60%. However, a variety of suitable porous materials may be used including an ultra high molecular weight polyolefin such as ultra high molecular weight polyethylene, porous polyethylene, porous polypropylene, and porous polyurethane. In one embodiment, the porous material has a node and fibril microstructure. The node and fibril microstructure, when present, is produced in the material using conventional methods. ePTFE and ultra high molecular weight polyethylene (also referred to as "expanded ultra high molecular weight polyethylene") typically have a node and fibril microstructure, and are not melt extrudable. However, a variety of suitable polymeric materials can be used in the method of the invention including conventional catheter balloon materials which are melt extrudable. Preferably, ePTFE is formed into a balloon layer by bonding wrapped layers of the polymeric material together to form a tubular member, and not by conventional balloon blow molding. Although discussed primarily in terms of the embodiment in which the first layer of the balloon comprises ePTFE, it should be understood that a variety of suitable polymers may be used for the first layer.

In a presently preferred embodiment, the outer surface of the porous polymeric material layer is modified by applying a polymer so that the polymer impregnates the pores of the porous polymeric material. This impregnating polymer is typically applied as a solution of the polymer in a suitable solvent, and the solvent evaporated to leave the impregnating polymer within the pores of the porous polymeric material. In one embodiment, the polymer is applied in an amount and at a concentration level sufficient to only partially fill the pores after evaporation of the solvent. However, the impregnating polymer may alternatively completely fill the pores of the porous polymeric material. Thus, the terminology "porous polymeric material" should be understood to include a material with pores partially or completely filled with an impregnating polymer. The porosity of the porous polymeric material typically drops from about 60% to about 95% before impregnation to about 0 to about 5% after impregnation. The coating density of the impregnating polymer in the pores of the porous polymeric material is typically about 0.7 mg/cm to about 1.2 mg/cm (i.e., weight of impregnating polymer per unit length of porous polymeric layer, after evaporation of the solvent of the impregnating polymer solution).

Preferably, the impregnating polymer is an elastomer, to minimize the affects on the balloon inflation and deflation characteristics. In a presently preferred embodiment, the impregnating polymer is a polyurethane copolymer such as Pursil (a silicone polyurethane copolymer) available from The Polymer Technology Group, and is preferably a soft polymer producing minimal affects on the balloon compliance. However, a variety of suitable polymers may be used which bond to the desired lubricious coating, including polyurethanes, dienes, styrene-isoprene-styrene block copolymers, C-flex (a siloxane modified polyolefin block copolymer), polybutylene methacrylic acid (PBMA), ethylene vinyl alcohol (EVAL), albumin, gelatin, polyamides including Elvamide, and PMMA. In a presently preferred embodiment, the polymer impregnating the porous polymeric material is the same polymer as the polymer forming the second (e.g., inner) layer of the balloon, to minimize the effect from the impregnating polymer on the compliance and flexibility of the balloon.

In a presently preferred embodiment, the outer surface of the porous polymeric material is cleaned, and preferably by exposing the outer surface to an inert gas plasma such as an argon plasma, before being impregnated with the impregnating polymer. However, alternative cleaning methods may be used including glow discharge or ethanol cleaning. The argon plasma cleaning provides improved bonding between the impregnating polymer and the porous polymeric material. Typically, the modified outer surface of the porous polymeric material is again cleaned with an inert gas plasma treatment after being modified (e.g., impregnated with the polymer) and before being coated with the lubricious compound.

In an alternative embodiment, the outer surface of the porous polymeric material layer is modified by depositing a functionality thereon. In one embodiment the deposited functionality is selected from the group consisting of a chemical solution etch functionality, a reactive gas plasma treatment functionality, and a plasma polymerized functionality. More specifically, in one embodiment, the deposited functionality is selected from the group consisting of a sodium naphthalate etch functionality, an ammonia plasma treatment amine group, a hydrogen plasma treatment hydroxyl group, and an acrylic acid plasma polymerized functionality. In the embodiment in which the modified surface is an etched surface, the etched surface is the result of a chemical reaction between the polymeric material forming the porous polymeric layer and the etching compound. For example, in the case of an ePTFE first layer and a sodium naphthalene etching solution, an activated form of sodium reacts with the ePTFE, resulting in the extraction of fluorine atoms from the surface of the ePTFE and the formation of a carbonaceous layer. The etched surface of the balloon has an increased surface energy compared to the balloon surface prior to being etched, for improved bondability to the lubricious coating. The terminology "etch" used herein in relation to the embodiment involving a plasma gas treatment should be understood to refer generally to the modification of the porous polymeric material which results from the gas-plasma treatment. In a presently preferred embodiment, the etching extends within the wall of the porous polymeric layer from the etched surface to a depth which is less than the wall thickness of the first layer. In one embodiment, the etching extends from the etched surface to a depth equal to about 0.5% to about 50%, more specifically about 1% to about 20% of a wall thickness of the first layer etched section (prior to inflation of the balloon). Alternatively, in the embodiment in which the modified surface is a plasma polymerized functionality, free-radical organic species, such as fragmented acrylic acid, in the plasma will couple with the surface of the porous polymeric material, resulting in a crosslinked thin film which is covalently bonded to the porous polymeric material. The plasma polymerized film may comprise a variety of suitable functionalities including carboxylate, amine, and sulfonate groups, which are polymerized on at least a surface of the porous polymeric material of the catheter balloon.

The outer surface of the porous polymeric material comprises a porous structure, so that the impregnating polymer or deposited functionality which modify the outer surface of the porous polymeric material are typically located in the pores and along at least part of the outer-most surface of the porous polymeric material.

In a presently preferred embodiment, the lubricious coating applied to the modified outer surface of the porous polymeric layer of the balloon comprises a hydrophilic compound. A variety of suitable conventional hydrophilic compounds may be used including polyethylene oxide (PEO), acrylate-PEO, and polyvinylpyrrolidone (PVP). The hydrophilic compound is typically applied as a solution of the hydrophilic compound in one or more solvents such as isopropyl alcohol, and optionally containing acrylates and polymerization photoinitiators, as is conventionally known. In an alternative embodiment, the lubricious coating comprises is a hydrophobic compound, including a silicone, or a fluorocarbon such as polytetrafluoroethylene (Teflon). The lubricious coating provides for improved catheter performance by increasing the lubricity of the outer surface of the balloon. In one embodiment, the porous polymer forming the outer layer of the balloon is itself a relatively lubricious polymer, such as for example a fluorocarbon, and in one embodiment is more lubricious than the polymer forming the inner layer of the balloon or at least a section of the catheter shaft. For example, fluorocarbons such as PTFE and ePTFE have a low surface energy of about 18 to about 22 dynes/cm, providing a low coefficient of friction of about 0.1 to about 0.15. The lubricious coating has a low surface energy providing a low coefficient of friction of about 0.01 to about 0.02. Thus, although fluorocarbons are generally considered to be relatively lubricious polymers, in the embodiment of the invention in which the balloon has an ePTFE or other fluorocarbon outer layer, the balloon has an improved lubricious surface due to the lubricious coating bonded to the outer low surface energy porous polymeric layer of the balloon.

A method of making a balloon catheter which embodies features of the invention generally includes modifying the outer surface of the porous polymeric layer of the balloon by impregnating the porous polymeric layer with a polymer, or is by depositing a functionality on the porous polymeric layer. Additionally, in a preferred embodiment, the inner surface of the porous polymeric layer is modified by depositing a functionality thereon, to improve bonding to the inner layer of the balloon. The inner surface of the porous polymeric layer is bonded to an outer surface of an inner layer of the balloon and the balloon is bonded to an elongated shaft so that an interior of the balloon is in fluid communication with an inflation lumen of the shaft. Preferably, the outer surface of the porous polymeric layer is modified before the layer is bonded to the inner layer of the balloon, to avoid any affects the modifying process may have on the inner layer. For example, in the embodiment in which the outer surface of the porous polymeric layer is impregnated with a polymer, the impregnation is preferably performed before bonding to the inner layer, to avoid the impregnation solution contacting (and potentially weakening) the inner layer. However, the outer surface of the porous polymeric layer can alternatively be modified after the layer is bonded to the inner layer of the balloon. The modified outer surface of the porous polymeric layer is coated with a lubricious compound, to form the balloon catheter having a lubricious balloon.

The balloon catheter of the invention has a balloon with a durable, highly lubricious coating on the outer surface of the balloon. The method of the invention provides an improved strong bond between the balloon and the lubricious coating, with improved manufacturability. These and other advantages of the invention will become more apparent from the following detailed description and accompanying exemplary figures.

DETAILED DESCRIPTION OF THE PREFERRED EMBODIMENTS

Figure 1:
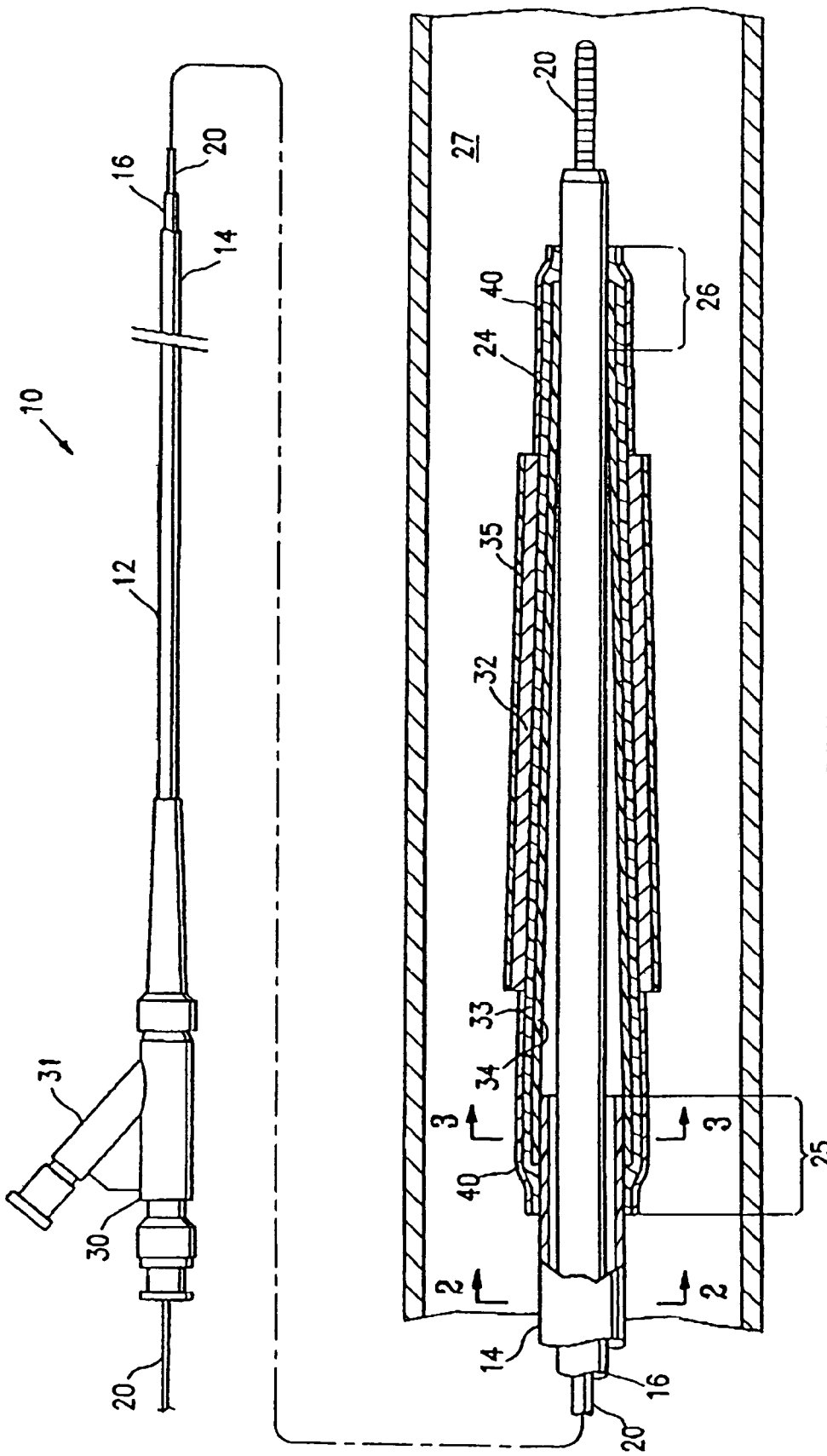
FIG. 1 is an elevational view, partially in section, of a stent delivery balloon catheter embodying features of the invention.
Figure 2:
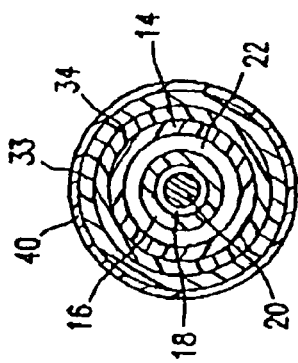
FIG. 2 is a transverse cross sectional view of the balloon catheter shown in FIG. 1, taken along line 2-2.
Figure 4:
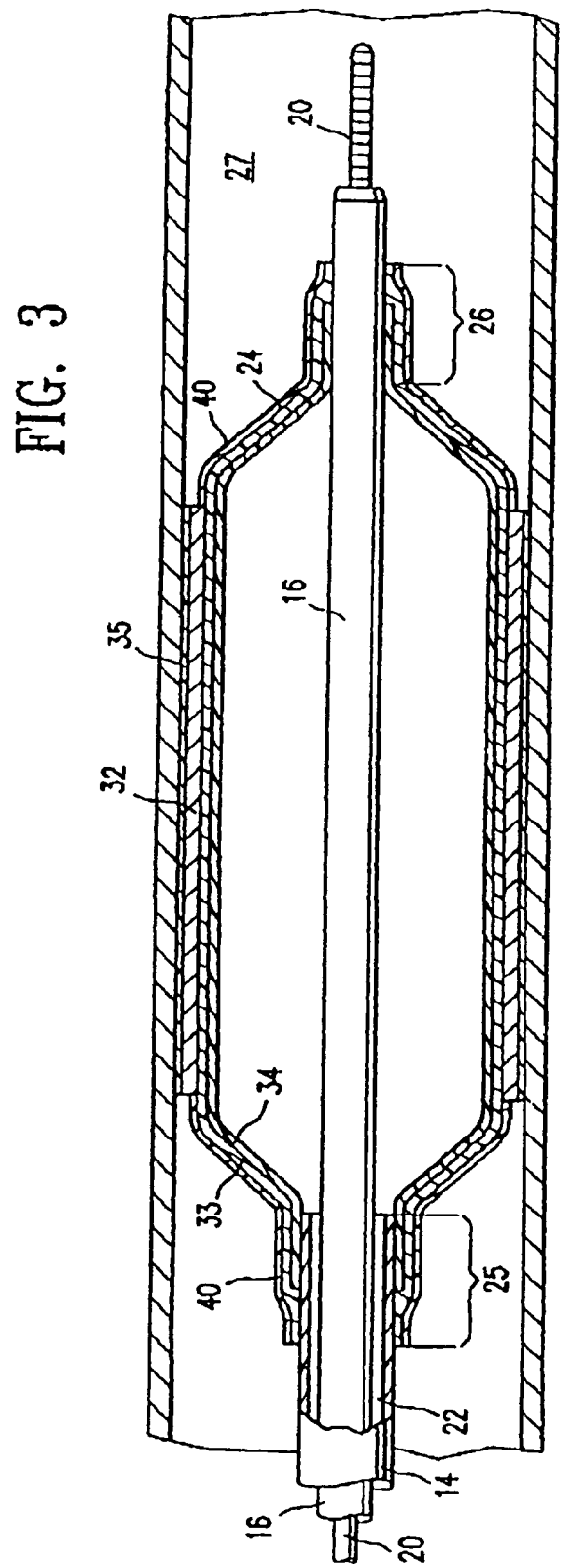
FIG. 4 illustrates the balloon catheter of FIG. 1, with the balloon in an inflated configuration to expand the stent within the patient's body lumen.

FIG. 1 illustrates an over-the-wire type stent delivery balloon catheter 10 embodying features of the invention. Catheter 10 generally comprises an elongated catheter shaft 12 having an outer tubular member 14 and an inner tubular member 16. Inner tubular member 16 defines a guidewire lumen 18 configured to slidingly receive a guidewire 20, and the coaxial relationship between outer tubular member 14 and inner tubular member 16 defines annular inflation lumen 22, as best shown in FIG. 2 illustrating a transverse cross section of the distal end of the catheter shown in FIG. 1, taken along line 2-2. An inflatable balloon 24 disposed on a distal section of catheter shaft 12 has a proximal skirt section 25 sealingly secured to the distal end of outer tubular member 14 and a distal skirt section 26 sealingly secured to the distal end of inner tubular member 16, so that the balloon interior is in fluid communication with inflation lumen 22. An adapter 30 at the proximal end of catheter shaft 12 is configured to provide access to guidewire lumen 18, and to direct inflation fluid through arm 31 into inflation lumen 22. In the embodiment illustrated in FIG. 1, the balloon 24 is illustrated prior to complete inflation thereof, with an expandable stent 32 having a stent cover 35 mounted on the working length of the uninflated balloon 24 for implanting within a patient's body lumen 27. The distal end of catheter 10 may be advanced to a desired region of the patient's body lumen 27 in a conventional manner, the balloon 24 inflated to expand covered stent 32, and the balloon deflated, leaving the covered stent 32 implanted in the body lumen 27. FIG. 4 illustrates the distal end of the balloon catheter of FIG. 1, with the balloon 24 fully inflated in the body lumen 27 to expand the covered stent 32.

In the embodiment of FIG. 1, balloon 24 has an outer layer 33 and an inner layer 34, extending the length of the balloon from the proximal skirt section 25 to the distal skirt section 26. The inner surface of the outer layer 33 is preferably bonded to the inner layer 34, as for example by fusion bonding and/or adhesive bonding, and the balloon 24 is preferably bonded to the shaft 12 preferably by fusion and/or adhesive bonding. For example, conventional adhesives such as light-cured (e.g., Dymax 204) and cyanoacrylates (e.g., Loctite 4011) may be used to bond layers 33, 34 to the shaft 12 at the proximal skirt section 25 and distal skirt section 26 of the balloon 24. In the embodiment illustrated in FIG. 1, the outer layer 33 of the balloon 24 has a proximal end section proximal to the inner layer 34 and bonded to the outer tubular member 14, and a distal end section distal to the inner layer 34 and bonded to the inner tubular member 16. The end sections of the outer layer 33, together with end sections of the inner layer 34 bonded to the shaft 12, form the proximal and distal skirt sections 25, 26, respectively. The proximal and distal skirt sections 25, 26 preferably have a length about equal to the minimum length required to provide a suitably strong bond between the balloon 24 and the shaft 12. The proximal end section and the distal end section of the inner layer 34 bonded to the shaft have a length of typically about 1 to about 5 mm, and the proximal end section and the distal end section of the outer layer 33 extending beyond the inner layer 34 and bonded to the shaft have a length of typically about 1 mm to about 4 mm, preferably about 1 mm to about 2 mm, for a balloon 24 having a length of about 8 to about 60 mm and a nominal outer diameter of about 2 to about 18 mm.

Balloon outer layer 33 comprises a porous polymeric material and in one preferred embodiment, a microporous polymeric material having a node and fibril microstructure, such as ePTFE. The inner layer 34 is formed of a polymeric material preferably different from the polymeric material of the outer layer 33. Preferably, the length of outer layer 33 in contact with inner layer 34 is bonded thereto. Inner layer 34 limits or prevents leakage of inflation fluid through the microporous ePTFE to allow for inflation of the balloon 24. The inner layer 34 is preferably formed of an elastomeric material to facilitate deflation of the balloon 24 to a low profile deflated configuration, including polyurethanes, silicone rubbers, polyamide block copolymers, dienes, and the like. The layer 34 may consist of a separate layer which neither fills the pores nor disturbs the node and fibril structure of the ePTFE layer 33, or it may at least partially fill the pores of the ePTFE layer 33. The ePTFE layer 33 is formed according to conventional methods, in which a sheet of ePTFE polymeric material is wrapped with overlapping or abutting edges to form a tubular body and then heated to fuse the wrapped material together. The sheet is typically wrapped to form one or more layers, and preferably about two to about five layers, of wrapped material which are heated to fuse the layers together. The sheet of polymeric material preferably has the desired microstructure (e.g., porous and/or node and fibril) before being wrapped on the mandrel. The resulting tube of ePTFE polymeric material is typically further processed by being stretched, sintered, compacted, and sintered again, to provide the desired properties such as the desired dimension, and dimensional stability (i.e., to minimize changes in length occurring during inflation of the balloon). The completed ePTFE layer 33 is then modified in accordance with the invention and bonded to or otherwise combined with elastomeric liner 34 either before or after layer 34 is bonded to the shaft.

Figure 3:
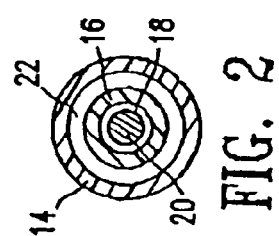
FIG. 3 is a transverse cross sectional view of the balloon catheter shown in FIG. 1, taken along line 3-3.

A lubricious coating 40 is bonded to the outer surface of the balloon 24. In the embodiment illustrated in FIG. 1, the lubricious coating 40 extends along less than the entire length of the outer layer 33, and specifically, is only located on the exposed outer surface of outer layer 33 on either end of the covered stent 32 and is not located along the portion of the central working length of the balloon on which the stent 32 is mounted. However, the lubricious coating 40 may be applied in a variety of suitable patterns to partially coat the outer surface of the porous polymeric outer layer 33, or alternatively to coat the entire outer surface of the outer layer 33, provided retention of the stent on the balloon working length is not compromised by the lubricious coating. The relative thickness of the coating 40 is exaggerated in FIG. 1 for ease of illustration. The thickness of the lubricious coating 40 is typically less than the wall thickness of the balloon 24, and specifically in one embodiment is about 1 to about 20 µm for a balloon having a wall thickness of about 0.05 to about 0.2 mm (0.002 to about 0.008 inches). The coating 40 preferably extends around the entire circumference of the coated section of the balloon 24, as best shown in FIG. 3 illustrating a transverse cross section of the balloon catheter of FIG. 1, taken along line 3-3.

The outer surface of the porous polymeric material forming outer layer 33 is modified in accordance with the invention to improve bondability of the lubricious coating 40 to the porous polymeric outer layer 33. In a presently preferred embodiment, the porous polymeric material is impregnated with an elastomeric polymer, such as for example a silicone polyurethane copolymer such as PURSIL, to form the modified outer surface. In one embodiment, the polymer used as the impregnating polymer (e.g., the silicone polyurethane) is the same as the polymer forming the inner layer 34 of the balloon 24 (i.e., the inner layer 34 comprises a silicone polyurethane). In a presently preferred embodiment, the entire length of the outer surface of the porous polymeric layer 33 is impregnated with the impregnating polymer, including the portion of the central working length which does not have the lubricious coating 40 thereon in the embodiment of FIG. 1. However, in alternative embodiments, only a portion(s) of the outer surface of the porous polymeric layer 33 is impregnated, such as for example only the portions to be subsequently coated with the lubricious coating 40.

The outer layer 33 of the balloon is typically impregnated by applying a solution of the impregnating polymer before being bonded to the inner layer 34 or the shaft 12. For example, a tube of a porous polymeric material (e.g., ePTFE) is preferably cleaned for example by argon plasma cleaning. Specifically, the tube is cleaned with argon plasma by subjecting the tube to the plasma at about 200 watts for about 5 minutes. A solution of PURSIL (75A) in THF, at a concentration of about 1 to about 5% PURSIL, is applied to the, outer surface of the cleaned porous polymeric tube, in one or more applications. For example, in one embodiment, a sponge is used to apply the solution in about 1 to about 5 applications. In one embodiment, enough solution to flood and saturate the surface of the ePTFE tube is applied to the tube. Sections of the porous polymeric tube may be masked to prevent impregnation thereof. For example, a polymeric covering such as a polymeric sheath with a length less than the length of the porous polymeric tube, is placed on the polymeric tube, tightly fitting thereon, before the tube is exposed to the impregnation solution. The sheath prevents the solution from contacting the outer surface of the porous polymeric tube covered by the sheath. Similarly, a tightly fitting mandrel may be used in the inner lumen of the porous polymeric tube to mask sections of the inner surface of the porous polymeric tube. The porous polymeric tube, wet with the solution, is then dried at about 40° C. for about 15 minutes to evaporate the solution solvent, leaving the PURSIL polymer impregnated in the porous polymeric tube. The porous polymeric tube having a thus modified outer surface is then positioned on the inner layer 34, either before or after the inner layer 34 is bonded to the shaft 12, and is bonded to the inner layer 34 and to the shaft 12 to form catheter 10. The porous polymeric tube may be further processed or modified prior to bonding to inner layer 34. For example, in one embodiment, the outer layer 33 of the balloon 24 has an inner surface which is gas plasma-etched/treated or chemical solution-etched along at least a section of the length of the outer layer 33 to improve bonding to the inner layer 34. With the balloon 24 secured to the shaft 12, a solution of a lubricious compound is applied to the impregnated outer surface of the outer layer 33 to form lubricious coating 40, typically after cleaning the outer surface of impregnated outer layer 33 as for example with an inert gas plasma such as an argon plasma. A variety of suitable conventional lubricious (e.g., hydrophilic) compound solutions may be used, and in one embodiment are applied by wiping the surface of the catheter balloon with a sponge soaked in the lubricious compound solution.

In an alternative embodiment, the modified outer surface of the porous polymeric layer 33 is formed by depositing a functionality on the porous polymeric layer, for example by treating the outer surface with a treatment selected from the group consisting of chemical solution etching, plasma gas etching, and plasma polymerization deposition. Sections of the porous polymeric tube may be masked to prevent etching of the sections, as discussed above. The chemical solution etching process typically comprises dipping or otherwise exposing the outer surface of the porous polymeric tube in a chemical etch solution. The duration of the exposure of the tube to the etching solution is carefully controlled to limit the depth of the etching within the wall of the tube, although the etching solution reaction is typically a self-limiting reaction. After removal from the etching solution, the porous polymeric tube is typically dipped or otherwise rinsed in a solution such as isopropyl alcohol to quench/deactivate any remaining etching solution thereon. The quenching solution is then rinsed using warm water and the resulting etched tube is dried. In one embodiment in which the outer surface of the porous polymeric is chemical solution etched, the chemical etched surface is provided by exposing the outer surface of a tube of the porous polymeric material to a sodium-naphthalate chemical etch solution. For example, in one embodiment the porous polymeric layer is etched using the following process. About 10-30 ml of about 10 to about 18 weight % sodium naphthalene in diethylene glycol dimethyl ether (2-methoxyethyl ether) solvent, available from Acton Technologies, Inc. under the trade name FluoroEtch Safety Solvent, is poured into a container and heated in a warm water bath (at about 37° C. or more). A porous polymeric tube having a length of about 8 cm is tightly fit on a mandrel and the entire porous polymeric tube is dipped in the etch solution for about 45±15 seconds with constant agitation. About 10 sheathed porous polymeric tubes may be treated at the same time using the same etch solution. The porous polymeric tube is removed from the solution and drained for a minimum of about 5 seconds, and soaked in 20 ml of 100% isopropyl alcohol for about 5 to about 30 seconds at room temperature to deactivate the etch solution. The porous polymeric tube is then washed in a warm water bath, which may be mildly acidic (not lower than pH 4), for about 1 minute. The acidity may be provided by acetic acid, to neutralize alkalinity of the etchant residue, provide fast effective cleaning, and contribute more acidic sites to the modified porous polymeric surface for improved bonding to basic adhesives. The porous polymeric tube is then air dried, or hot air dried at about 70° C. to about 75° C. for at least about 15 minutes. The resulting modified outer layer 33 is then coated with the lubricious compound to produce lubricious coating 40 as set forth above.

In an alternative embodiment, the modified outer surface of the outer layer 33 is prepared using a gas plasma etch/treatment, such as an ammonia gas plasma treatment. In the ammonia gas plasma treatment, the surface is treated with ammonia anions by reaction in an ammonia gas filled plasma chamber, to deposit an amine functionality on the surface of the porous polymeric material. Alternative gases may be used in the gas plasma etching in addition to or instead of the ammonia gas. For example, in one embodiment the porous polymeric layer is gas plasma etched using the following process. The porous polymeric tube is provided in a plasma chamber having ammonia gas at a pressure of about 80 to about 90 mtorr. In a presently preferred embodiment, in addition to the reactive species formed by the ammonia, hydrogen gas ($H_2$) in the chamber with the ammonia gas forms reactive species. The concentration of hydrogen is about 1% to about 50%. Specifically, in one embodiment, the plasma chamber has 99% ammonia, and 1% hydrogen, at a pressure of about 86 mTorr. The porous polymeric tube is exposed to the ammonia plasma for about 1 to about 5 minutes, typically about 3 to 5 minutes, with the ammonia plasma generated at a power of about 450 watts. The resulting modified outer layer 33 is then coated with the lubricious compound to produce lubricious coating 40, as set forth above.

In an alternative embodiment, the modified outer surface of outer layer 33 is prepared by depositing a plasma polymerized functionality. In a presently preferred embodiment, the modified outer surface is a plasma polymerized carboxylate film comprising an acrylate or acrylate-like polymer layer deposited onto the porous polymeric tube by exposing the porous polymeric tube to a plasma, which in a presently preferred embodiment is an acrylic acid plasma. One of skill in the art will recognize that some fragmentation of the acrylate typically occurs as the result of plasma polymerization, producing an acrylate-like polymer layer of fragmented acrylate. The resulting modified outer layer 33 is then coated with the lubricious compound to produce lubricious coating 40, as set forth above.

The dimensions of catheter 10 are determined largely by the size of the balloon and guidewire to be employed, the catheter type, and the size of the artery or other body lumen through which the catheter must pass or the size of the stent being delivered. Typically, the outer tubular member 14 has an outer diameter of about 0.025 to about 0.04 inch (0.064 to 0.10 cm), usually about 0.037 inch (0.094 cm), and the wall thickness of the outer tubular member 14 can vary from about 0.002 to about 0.008 inch (0.0051 to 0.02 cm), typically about 0.003 to 0.005 inch (0.0076 to 0.013 cm). The inner tubular member 16 typically has an inner diameter of about 0.01 to about 0.018 inch (0.025 to 0.046 cm), usually about 0.016 inch (0.04 cm), and a wall thickness of about 0.003 to about 0.008 inch (0.007 to 0.02 cm). The overall length of the catheter 10 may range from about 100 to about 150 cm, and is typically about 143 cm. Preferably, balloon 24 has a length about 0.8 cm to about 6 cm, and an inflated working diameter of about 2 to about 10 mm, more specifically about 2.5 to about 5 mm.

Inner tubular member 16 and outer tubular member 14 can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. In the embodiment illustrated in FIG. 1, the outer and inner tubular members 14, 16 are each formed of a single-layered, uniform polymeric member. However, it should be understood that in alternative embodiments, one or both of the outer and inner tubular members 14, 16 may be a multilayered or blended polymeric member. Although the shaft is illustrated as having an inner and outer tubular member, a variety of suitable shaft configurations may be used including a dual lumen extruded shaft having a side-by-side lumens extruded therein. Similarly, although the embodiment illustrated in FIG. 1 is an over-the-wire stent delivery catheter, balloons of this invention may also be used with other types of intravascular catheters, such as rapid exchange type balloon catheters.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. A method of making a balloon catheter having a lubricious balloon, comprising:
   (a) modifying an outer surface of a porous polymeric layer of a balloon by applying a solution of a polymer onto the outer surface of the porous layer to impregnate the porous polymeric layer with the polymer, or by depositing a functionality on the porous polymeric layer before bonding the porous polymeric layer to the inner layer of the balloon;
   (b) modifying an inner surface of the porous polymeric layer by depositing a functionality on the porous polymeric layer;
   (c) bonding the inner surface of the porous polymeric layer to an outer surface of the inner layer of the balloon and bonding the balloon to an elongated shaft so that an interior of the balloon is in fluid communication with an inflation lumen of the shaft; and
   (d) coating the modified outer surface of the porous polymeric layer of the balloon with a lubricious compound, so that the modified outer surface bonds to the lubricious compound, to form the balloon catheter having a lubricous balloon.

2. The method of claim 1 including cleaning the outer surface of the porous polymeric layer before impregnation, by exposing the outer surface to an argon plasma treatment.

3. The method of claim 1 wherein depositing the functionality on the outer surface of the porous polymeric layer comprises treating the outer surface with a treatment selected from the group consisting of chemical solution etching, plasma gas etching, and plasma polymerization deposition.

4. A method of making a balloon catheter having a lubricious balloon, comprising:
   a) modifying an outer surface of a porous polymeric layer of a balloon by applying a solution of a polymer onto the outer surface of the porous polymeric layer to impregnate the porous polymeric layer with the polymer;
   b) bonding an inner surface of the porous polymeric layer to an outer surface of an inner layer of the balloon and bonding the balloon to an elongated shaft so that an interior of the balloon is in fluid communication with an inflation lumen of the shaft; and
   c) coating the modified outer surface of the porous polymeric lubricious layer of the balloon with a lubricious compound, so that the modified outer surface bonds to the lubricious compound, to form the balloon catheter having a lubricious balloon.

5. The method of claim 4 wherein the impregnating solution is applied to the porous polymeric layer before the porous polymeric layer is bonded to the inner layer of the balloon and before the porous polymeric layer is bonded to the shaft.

6. The method of claim 4 wherein the lubricious compound is applied to a section of the modified outer surface having length less than the entire length of the modified outer surface, so that the lubricious balloon of the balloon catheter has the lubricious coating along less than the entire inflatable length of the balloon.

7. The method of claim 4 wherein the impregnating solution is applied to a portion of the layer having a length less than the entire length of the layer, so that the balloon has a first inflatable portion impregnated with the polymer solution and coated with the lubricious compound, and a second inflatable portion longitudinally adjacent thereto which is not impregnated with the polymer solution and which is not coated with a lubricious compound.

8. The method of claim 7 including, before the impregnating solution is applied, masking with a mask one or more portions of the balloon longitudinally adjacent to the portion to be impregnated and removing the mask after the impregnating solution is applied.

\* \* \* \* \*